US011364277B2

(12) United States Patent
Angeli et al.

(10) Patent No.: US 11,364,277 B2
(45) Date of Patent: Jun. 21, 2022

(54) TREATMENT OF ASCITES

(71) Applicant: BioVie Inc., Beverly, MA (US)

(72) Inventors: Paolo Angeli, Padua (IT); Penelope Markham, Clifton, VA (US); Jonathan Adams, Chicago, IL (US)

(73) Assignee: BioVie Inc., Santa Monica, CA (US)

( * ) Notice: Subject to any disclaimer, the term of this patent is extended or adjusted under 35 U.S.C. 154(b) by 0 days.

(21) Appl. No.: 16/379,446

(22) Filed: Apr. 9, 2019

(65) Prior Publication Data

US 2019/0365848 A1 Dec. 5, 2019

Related U.S. Application Data

(63) Continuation of application No. 15/491,613, filed on Apr. 19, 2017, now abandoned, which is a continuation of application No. 15/198,050, filed on Jun. 30, 2016, now Pat. No. 9,655,945.

(60) Provisional application No. 62/321,558, filed on Apr. 12, 2016, provisional application No. 62/267,510, filed on Dec. 15, 2015, provisional application No. 62/186,638, filed on Jun. 30, 2015.

(51) Int. Cl.
*A61K 38/095* (2019.01)
*A61P 1/16* (2006.01)
*A61P 1/00* (2006.01)

(52) U.S. Cl.
CPC .............. *A61K 38/095* (2019.01); *A61P 1/00* (2018.01); *A61P 1/16* (2018.01)

(58) Field of Classification Search
CPC ................................ A61K 38/095; A61P 1/16
See application file for complete search history.

(56) References Cited

U.S. PATENT DOCUMENTS

| | | | |
|---|---|---|---|
| 7,160,853 B2 | 1/2007 | Lebrec et al. | |
| 2004/0102362 A1* | 5/2004 | Lebrec ................. | A61K 38/095 514/1.1 |
| 2009/0305959 A1* | 12/2009 | Laporte ................... | A61P 11/00 514/1.1 |
| 2010/0311642 A1* | 12/2010 | Riviere ..................... | A61P 7/00 514/1.4 |
| 2011/0003890 A1* | 1/2011 | Schwartz ............... | A61K 33/30 514/491 |
| 2011/0237494 A1* | 9/2011 | Laporte .................... | A61P 9/00 514/1.4 |
| 2011/0300109 A1 | 12/2011 | Tepic et al. | |
| 2012/0157526 A1* | 6/2012 | Jalan ..................... | A61K 31/195 514/555 |
| 2013/0197044 A1* | 8/2013 | Pavliv ..................... | A61P 9/00 514/374 |
| 2014/0147875 A1 | 5/2014 | Everson et al. | |
| 2014/0329747 A1* | 11/2014 | Tidmarsh ............. | A61K 31/165 514/9.7 |
| 2014/0378660 A1 | 12/2014 | Short et al. | |
| 2015/0056194 A1 | 2/2015 | Hsu | |
| 2015/0126432 A1 | 5/2015 | Wisniewski et al. | |

FOREIGN PATENT DOCUMENTS

WO     WO 2013/106072     7/2013

OTHER PUBLICATIONS

Robertson et al., 2014, Continuous Outpatient Terlipressin Infusion for Hepatorenal Syndrome as a Bridge to Successful Liver Transplantation, Hepatology, 60(6): 2125-2126.*
Angeli, 2013, Terlipressin for the treatment of hepatorenal syndrome in patients with cirrhosis, Expert Opinion on Orphan Drugs, 1(3): 241-248.*
Fimiani et al., 2011, The use of terlipressin in cirrhotic patients with refractory ascites and normal renal function: A multicentric study, European Journal of Internal Medicine, 22: 587-590.*
Alessandria et al., "Noradrenalin vs terlipressin in patients with hepatorenal syndrome: A prospective, randomized, unblinded, pilot study," Journal of Hepatology, 47:499-505 (2007).
Alessandria et al., "Renal failure in cirrhotic patients: role of terlipressin in clinical approach to hepatorenal syndrome type 2," European Journal of Gastroenterology & Hepatology, 14:1363-1368 (2002).
Alessandria et al., "MELD Score and Clinical Type Predict Prognosis in Hepatorenal Syndrome: Relevance to Liver Transplantation," Hepatology, 41:1282-89 (2005).
Ali et al., "Clinical Study on the Therapeutic Role of Midodrine in Non azotemic Cirrhotic Patients with Tense Ascites: A Double-Blind, Placebo-Controlled, Randomized Trial," Hepato-Gastroenterology, 61:1915-1925 (2014).
Angeli et al., "Hyponatremia in Cirrhosis: Results of a Patient Population Survey," Hepatology, 44:1525-1542 (2006).
Angeli, et al., "Terlipressin Given as Continuous Intravenous Infusion Versus Terlipressin Given as Intravenous Boluses In the Treatment of Type 1 Hepatorenal Syndrome (HRS) in Patients With Cirrhosis," Journal of Hepatology, Abstract 175 of the 44th Annual Meeting of the European Association for the Study, vol. 50, Supplement 1 (2009).
Angeli, P., "Terlipressin for Hepatorenal Syndrome: Novel Strategies and Future Perspectives," Ascites, Hyponatremia and Hepatorenal Syndrome: Progress in Treatment, 28:189-197 (2011).
Angeli, "Terlipressin for the treatment of hepatorenal syndrome in patients with cirrhosis" Expert Opinion on Orphan Drugs, 1(3):241-48 (2013).
Bari et al., "The Combination of Octreotide and Midodrine Is Not Superior to Albumin in Preventing Recurrence of Ascites After Large-Volume Paracentesis," Clinical Gastroenterology and Hepatology, 10:1169-1175 (2012).
Caraceni et al., "Long-term treatment of hepatorenal syndrome as a bridge to liver transplantation," Digestive and Liver Disease, 43:242-245 (2011).

(Continued)

*Primary Examiner* — Amber D Steele
(74) *Attorney, Agent, or Firm* — McDonnell Boehnen Hulbert & Berghoff LLP

(57) ABSTRACT

A method for treating ascites patients by administering the peptide drug terlipressin by continuous infusion. The patients include those whose ascites condition has not progressed to hepatorenal syndrome (HRS). Administration may be accomplished with a continuous infusion pump.

18 Claims, No Drawings

(56) References Cited

OTHER PUBLICATIONS

Cavallin et al., "Terlipressin Given by Continuous Intravenous Infusion Versus Intravenous Boluses in the Treatment of Hepatroenal Syndrome: A Randomized Controlled Study," Hepatology, 63(3):983-992 (2016).

Cavallin et al., "Terlipressin plus albumin versus midodrine and octreotide plus albumin in the treatment of hepatorenal syndrome: a randomized trial," Hepatology, 62(2):567-574 (2015).

Cervoni, M.D., Jean Paul et al., "Terlipressin May Influence the Outcome of Hepatorenal Syndrome Complicating Alcoholic Hepatitis," Am. J. Gastroenterol., 92(11):2113-2114 (1997).

Curriculum Vitae of Prof Paul J. Gow. Exhibit 1003 in *Mallinckrodt* v. *BioVie* IPR2018-00974, filed by Mallinckrodt Apr. 27, 2018, pp. 1-17.

Declaration of Paul Gow Under 37 C.F.R. §1.68 in Support of Petition for Inter Partes Review of U.S. Pat. No. 9,655,945. Exhibit 1002 in *Mallinckrodt* v. *BioVie* IPR2018-00974, filed by Mallinckrodt Apr. 27, 2018, pp. 1-90.

Ding et al., "Hemodynamic effects of continuous versus bolus infusion of terlipressin for portal hypertension: A randomized comparison," Gastroenterology and Hepatology, 28:1242-1246 (2013).

Döhler, Klaus D., "Terlipressin and Hyponatremia," A short review, Curatis Pharma GmbH, (Oct. 31, 2010) (6 pages).

Fabrizi et al., "Terlipressin for hepatorenal syndrome: A meta-analysis of randomized trials," The International Journal of Artificial Organs, 32(3):133-140 (2009).

Fernández-Varo et al., "Vasopressin 1a Receptor Partial Agonism Increases Sodium Excretion and Reduces Portal Hypertension and Ascites in Cirrhotic Rats," Hepatology, 63(1):207-216 (2016).

Fiamiani et al., "The use of terlipressin in cirrhotic patients with refractory ascites and normal renal function: A multicentric study," European Journal of Internal Medicine, 22:587-590 (2011).

Gadano et al., "Natriuretic response to the combination of atrial natriuretic peptide and terlipressin in patients with cirrhosis and refractory ascites," Journal of Hepatology, 26:1229-1234 (1997).

Ganne-Carrié, M.D., Nathalie et al., "Hepatorenal Syndrome Long-Term Treatment with Terlipressin as a Bridge to Liver Transplantation," Disgestive Diseases and Sciences, 41(6):1054-1056 (Jun. 1996).

Gentilini et al., "Albumin Improves the Response to Diuretics in Patients with Cirrhosis and Ascites: Results of a Randomized, Controlled Trial," Journal of Hepatology, 30:639-45 (1999).

Gerbes et al., "Terlipressin for Hepatorenal Syndrome: Continuous Infusion as an Alternative to IV Bolus Administration, with replies by Sanyal & Boyer and Ginès et al.," Gastroenterology, 137:1179-1181. Exhibit 2026 in *Mallinckrodt* v. *BioVie* IPR2018-00974, filed by BioVie on Mar. 7, 2019.

Ghosh et al., "Noradrenaline vs terlipressin in the treatment of type 2 hepatorenal syndrome: a randomized pilot study," Liver International, 33(8):1187-1193 (2013).

Gines et al., "Incidence, Predictive Factors, and Prognosis of the Hepatorenal Syndrome in Cirrhosis With Ascites," Gastroenterology, 105:229-236 (1993).

Gluud et al., "Systematic Review of Randomized Trials on Vasoconstrictor Drugs for Hepatorenal Syndrome," Hepatology, 51(2):576-584 (Feb. 2010).

Gluud et al., "Terlipressin for hepatorenal syndrome (Review)," The Cochrane Collaboration, 12(9):1-35 (2012).

Gordon, "Ascites," Clin. Liver Dis., 16:285-299 (2012).

Gow et al., "Outpatient Terlipressin Infusion for the Treatment of Refractory Ascites," The American Journal of Gastroenterology, 111:1041-1042 (Jul. 2016).

Hsu, Shao-Jung and Huang, Hui-Chun, "Management of ascites in patients with liver cirrhosis: Recent evidence and controversies," Journal of the Chinese Medical Association, 76:123-130 (2013).

Huang, Y-Y et al., "Terlipressin Resolves Ascites of Cirrhotic Rats through Downregulation of Aquaproin 2," The Journal of International Medical Research, 40:1735-1744 (2012).

Jarcuska et al., "Hemodialysis in Hepatorenal Syndrome Type 1 in Alcoholic Liver Cirrhosis Treated by Continual Terlipressin Infusion in Combination with Albumin Plasmaexpansion," Hepatology, 38(S2):194-195 (2003).

Jarcuska et al., "Hepatorenal Syndrome Type 1 in Patients with Acute Alcoholic Hepatitis Treated with Continual Terlipressin Infusion in Combination with Albumin Plasmaexpansion," Hepatology, 36(S1):256 (2002).

Kalambokis et al., "Effects of somatostatin, terlipressin and somatostatin plus terlipressin on portal and systemic hemodynamics and renal sodium excretion in patients with cirrhosis," Journal of Gastroenterology and Hepatology, 20:1075-1081 (2005).

Kalambokis et al., "Effects of terlipressin on water excretion after oral water load test in nonazotemic cirrhotic patients with ascites without hyponatremia," Scandinavian Journal of Gastroenterology, 45(12):1509-1515 (2010).

Kalambokis et al., "Vasoconstrictor Therapy for Patients with Cirrhosis with Ascites but Without Hepatorenal Syndrome," Hepatology, 48(2):686 (2008).

Krag et al., "Terlipressin Improves Renal Function in Patients with Cirrhosis and Ascites Without Hepatorenal Syndrome," Hepatology, 46:1863-1871 (2007).

Krag, Aleksander, "Efficacy and Safety of Terlipressin in Cirrhotic Patients and Variceal Bleeding or Hepatorenal Syndrome," Adv. Ther., 25(11):1105-1140 (2008).

Lange et al., "Continuous Versus Bolus Infusion of Terlipressin in Ovine Endotoxemia," Shock, 28(5) (2007) (8 pages).

Lenaerts et al., "Comparative pilot study of repeated large volume paracentesis vs the combination on clonidine-spironolactone in the treatment of cirrhosis-associated refractory ascites," Gastroenterol Clin Biol, 29(11):1137-1142 (2005).

Lim et al., "Vasoconstrictor Therapy for the Hepatorenal Therapy," Gastroenterology, 134:1608-11 (2008).

Martín-Llahí et al., "Terlipressin and Albumin vs Albumin in Patients With Cirrhosis and Hepatorenal Syndrome: a Randomized Study," Gastroenterology, 134:1352-1359 (2008).

Moreau et al., "Clinical characteristics and outcome of patients with cirrhosis and refractory ascites," Liver International, 24:457-464 (2004).

Morelli et al., "Continuous terlipressin versus vasopressin infusion in septic shock (TERLIVAP): a randomized, controlled pilot study," Critical Care, vol. 13 (2009) (14 pages).

Mulkay et al., "Long-term terlipressin administration improves renal function in cirrhotic patients with type 1 hepatorenal syndrome: a pilot study," Acta Gastro-Enterologica Belgica, 64:15-19 (Jan.-Mar. 2001).

Neri et al., "Terlipressin and Albumin in Patients with Cirrhosis and Type 1 Hepatorenal Syndrome," Dig. Dis. Sci., 53:830-835 (2008).

Nilsson et al., "Pharmacokinetics of Terlipressin After Single I.V. Doses to Healthy Volunteers," Drugs Exptl Clin. Res., 16(6):307-314 (1990).

Ortega et al., "Terlipressin Therapy With and Without Albumin for Patients With Hepatorenal Syndrome: Results of a Prospective, Nonrandomized Study," Hepatology, 36:941-948 (Oct. 2002).

Parry, "Terlipressin and Albumin Combination Therapy Improves Renal Function in HRS-1," Peer-Reviewed Highlights from AASLD: The Liver Meeting, pp. 17-18 (Dec. 2014).

Petitioner's Request for Oral Argument. Paper 24 in *Mallinckrodt* v. *BioVie* IPR2018-00974, filed by Mallinckrodt on Jul. 15, 2019, pp. 1-5.

Petitioner's Sur-Reply to Patent Owner's Reply in Support of Its Contingent Motion to Amend. Paper 25 in *Mallinckrodt* v. *BioVie* IPR2018-00974, filed by Mallinckrodt on Jul. 15, 2019, pp. 1-18.

United States Patent and Trademark Office. Order, Conduct of the Proceeding, 37 C.F.R. § 42.5, dated Jul. 16, 2019. Paper 26 in *Mallinckrodt* v. *BioVie* IPR2018-00974, pp. 1-3.

United States Patent and Trademark Office. Order, Oral Hearing, 37 C.F.R. § 42.70, dated Jul. 17, 2019. Paper 27 in *Mallinckrodt* v. *BioVie* IPR2018-00974, pp. 1-6.

Petitioner's Motion to Strike Portions of Patent Owner's Sur-Reply. Paper 28 in *Mallinckrodt* v. *BioVie* IPR2018-00974, filed by Mallinckrodt on Jul. 22, 2019, pp. 1-4.

(56) References Cited

OTHER PUBLICATIONS

Patent Owner's Opposition to Petitioner's Motion to Strike Portions of Patent Owner's Sur-Reply. Paper 29 in *Mallinckrodt* v. *BioVie* IPR2018-00974, filed by BioVie on Jul. 29, 2019, pp. 1-8.
United States Patent and Trademark Office. Record of Oral Hearing held on Aug. 12, 2019. Paper 30 in *Mallinckrodt* v. *BioVie* IPR2018-00974, issued on Sep. 4, 2019, pp. 1-73.
United States Patent and Trademark Office. Order, Conduct of the Proceeding, 37 C.F.R. § 42.5, dated Oct. 11, 2019. Paper 31 in *Mallinckrodt* v. *BioVie* IPR2018-00974, pp. 1-3.
Patent Owner's Notice of Supplemental Authority. Paper 32 in *Mallinckrodt* v. *BioVie* IPR2018-00974, filed by BioVie on Oct. 16, 2019, pp. 1-5.
Petitioner's Reply to Patent Owner's Notice of Supplemental Authority. Paper 33 in *Mallinckrodt* v. *BioVie* IPR2018-00974, filed by Mallinckrodt on Oct. 21, 2019, pp. 1-5.
United States Patent and Trademark Office. Final Written Decision, dated Nov. 13, 2019. Paper 34 in *Mallinckrodt* v. *BioVie* IPR2018-00974, pp. 1-77.
Petitioner Email to the Board dated Jul. 12, 2019. Exhibit 3001 in *Mallinckrodt* v. *BioVie* IPR2018-00974, 1 page.
Patent Owner Email to the Board dated Oct. 10, 2019. Ex. 3002 in *Mallinckrodt* v. *BioVie* IPR2018-00974, 1 page.
Patent Owner's Preliminary Response Under 37 C.F.R. § 42.107. Paper 6 in *Mallinckrodt* v. *BioVie* IPR2018-00974, filed by BioVie on Aug. 15, 2018, pp. 1-45.
Petition for Inter Partes Review of U.S. Pat. No. 9,655,945 Under 35 U.S.C. §§ 311 et seq. and 37 C.F.R. § 42.100 et seq. Paper 2 in *Mallinckrodt* v. *BioVie* IPR2018-00974, filed by Mallinckrodt on Apr. 27, 2018, pp. 1-72.
PharmaIN Press Release, FDA Grants Orphan-Drug Designation for Novel Terlipressin Formulation for the Treatment of Ascites, PharmaIN website (Apr. 1, 2013), available at: http://pharmain.com/fda-grants-orphan-drugdesignation-for-novel-terlipressin-formulation-for-thetreatment-of-ascites (2 pages).
Piano et al., "Continuous recurrence of type 1 hepatorenal syndrome and long-term treatment with terlipressin and albumin: A new exception to MELD score in the allocation system to liver transplantation?" Journal of Hepatology, 55:491-496 (2011).
Planas et al., "Natural History of Patients Hospitalized for Management of Cirrhotic Ascites," Clinical Gastroenterology & Hepatology, 4:1385-94 (2006).
Robertson et al., "Continuous Outpatient Terlipressin Infusion for Hepatorenal Syndrome as a Bridge to Successful Liver Transplantation," Hepatology, 60(6):2125-2126 (2014).
Rodriguez et al., "Treatment of Type 2 Hepatorenal Syndrome in Patients Awaiting Transplantation: Effects on Kidney Function and Transplantation Outcomes," Liver Transplantations, 21:1347-1354 (2015).
Runyon, M.D., Bruce A., "Management of Adult Patients with Ascites Due to Cirrhosis: Update 2012," AASLD Practice Guideline, Hepatology, pp. 1-27 (Feb. 2013).
Sagi et al., "Terlipressin therapy for reversal of type 1 hepatorenal syndrome: A meta-analysis of randomized controlled trials," Journal of Gastroenterology and Hepatology, 25(5):880-885 (2010).
Salerno et al., "Diagnosis, Prevention and Treatment of Hepatorenal Syndrome in Cirrhosis," Gut, 56(9):1310-1318 (2007).
Saner et al., "Terlipressin plus hydroxyethyl starch infusion: an effective treatment for hepatorenal syndrome," European Journal of Gastroenterology & Hepatology, 15:925-927 (2003).
Sanyal et al., "A Randomized, Prospective, Double-Blind, Placebo-Controlled Trial of Terlipressin for Type 1 Hepatorenal Syndrome," Gastroenterology, 134:1360-1368 (2008).
Singh et al., "Midodrine and Clonidine in Patients With Cirrhosis and Refractory or Recurrent Ascites: A Randomized Pilot Study," The American Journal of Gastroenterology, 108:560-567 (Apr. 2013).
Singh et al., "Midodrine in patients with cirrhosis and refractory or recurrent ascites: A randomized pilot study," Journal of Hepatology, 56:348-354 (2012).

Siqueira et al., "Refractory Ascites: Pathogeneis, Clinical Impact, and Management," Gastroenterology & Hepatology, 5(9):647-56 (Sep. 2009).
Sola et al., "Hyponatremia in Patients Treated With Terlipressin for Severe Gastrointestinal Bleeding Due to Portal Hypertension," Hepatology, 52:1783-90 (2010).
Solanki et al., "Beneficial effects of terlipressin in hepatorenal syndrome: A prospective, randomized placebo-controlled clinical trial," Journal of Gastroenterology and Hepatology, 18:152-56 (2003).
Tandon et al., "The effect of 1 month of therapy with midodrine, octreotide-LAR and albumin in refractory ascites: a pilot study," Liver International, 29(2):169-74 (Feb. 2009).
Therapondos et al., "Systemic, portal and renal effects of terlipressin in patients with cirrhotic ascites: Pilot Study," Journal of Gastroenterology and Hepatology, 19:73-77 (2004).
Vasudevan et al., "Efficacy of outpatient continuous terlipressin infusions for hepatorenal syndrome," Hepatology, 5 pages (2015).
Wong et al., "Effects of a selective vasopressin V2 receptor antagonist, satavaptan, on ascites recurrence after paracentesis in patients with cirrhosis," Journal of Hepatology, 53:283-90 (2010).
Wong et al., "Midodrine, Octreotide, Albumin, and TIPS in Selected Patients With Cirrhosis and Type 1 Hepatorenal Syndrome," Hepatology, 40:55-64 (2004).
Wong et al., "Working Party proposal for a revised classification system of renal dysfunction in patients with cirrhosis," Gut, 60:702-709 (2011).
Wong, "Management of ascites in cirrhosis," Journal of Gastroenterology and Hepatology, 27:11-20 (2012).
Abe & Miyasaka, Kidney and Dialysis, 70(3):361-66 (2011). (in Japanese).
English translation of Notice for Reasons for Rejection in JP Patent Application No. 2018-145654; dated Jul. 10, 2019, pp. 1-3 (describing Abe & Miyasaka, Kidney and Dialysis, 70(3):361-66 (2011)).
The CONFIRM Study, "A Study to Confirm Efficacy and Safety of Terlipressin in HRS Type 1," ClinicalTrials.gov, Summary, available at clinicaltrials.gov/ct2/show/NCT02770716?term=terlipressin&recrs=abc (first posted May 12, 2016). Exhibit 2005 in *Mallinckrodt* v. *BioVie* IPR2018-00974, filed by BioVie on Aug. 15, 2018, pp. 1-7.
Mallinckrodt Press Release, "First Patient Enrolled in Mallinckrodt Phase 3 Terlipressin Trial," available at www.prnewswire.com/news-releases/first-patient-enrolled-inmallinckrodt-phase-3-terlipressin-trial-300305910.html (Jul. 28, 2016). Exhibit 2006 in *Mallinckrodt* v. *BioVie* IPR2018-00974, filed by BioVie on Aug. 15, 2018, pp. 1-5.
FDA, "What is a Serious Adverse Event?," available at web.archive.org/web/20150504051703/https://www.fda.gov/safety/medwatch/howtoreport/ucm053087.htm (last updated Jan. 10, 2014). Exhibit 2007 in *Mallinckrodt* v. *BioVie* IPR2018-00974, filed by BioVie on Aug. 15, 2018, pp. 1-2.
Transcript of the Deposition of Dr. Jaime Bosch, dated May 9, 2019. Exhibit 1016 in *Mallinckrodt* v. *BioVie* IPR2018-00974, filed by Mallinckrodt on Jun. 4, 2019, pp. 1-150.
Rebuttal Declaration of Paul Gow Under 37 C.F.R. § 1.68 in Support of Petitioner's Reply. Exhibit 1017 in *Mallinckrodt* v. *BioVie* IPR2018-00974, filed by Mallinckrodt on Jun. 4, 2019, pp. 1-9.
Romanelli et al., "Long-term albumin infusion improves survival in patients with cirrhosis and ascites: An unblended randomized trial" World Journal of Gastroenterology, 12(9):1403-1407 (2006). Exhibit 1019 in *Mallinckrodt* v. *BioVie* IPR2018-00974, filed by Mallinckrodt on Jun. 4, 2019.
Testro et al., "Long-term outcome of patients treated with terlipressin for types 1 and 2 hepatorenal syndrome," Hepatology, 23:1535-1540 (2008). Exhibit 2022 in *Mallinckrodt* v. *BioVie* IPR2018-00974, filed by BioVie on Mar. 7, 2019.
Declaration of Dr. Jaime Bosch, MD, PhD Under 37 C.F.R. § 1.68 in Support of Patent Owner's Response. Exhibit 2023 in *Mallinckrodt* v. *BioVie* IPR2018-00974, filed by BioVie on Mar. 7, 2019, pp. 1-104.
Dr. Jaime Bosch's Curriculum Vitae. Exhibit 2024 in *Mallinckrodt* v. *BioVie* IPR2018-00974, filed by BioVie on Mar. 7, 2019, pp. 1-10.

(56) References Cited

OTHER PUBLICATIONS

Ginès et al., "EASL clinical practice guidelines on the management of ascites, spontaneous bacterial peritonitis, and hepatorenal syndrome in cirrhosis," Journal of Hepatology, 53:397-417 (2010). Exhibit 2027 in *Mallinckrodt v. BioVie* IPR2018-00974, filed by BioVie on Mar. 7, 2019.
Ganne-Carrié et al., "Hepatorenal Syndrome: Long-term treatment with terlipressin as a bridge to liver transplantation," Digestive Diseases and Sciences, 41(6):1054-56 (1996). Exhibit 2028 in *Mallinckrodt v. BioVie* IPR2018-00974, filed by BioVie on Mar. 7, 2019.
Moreau and Lebrec, "The use of vasoconstrictors in patients with cirrhosis: type 1 HRS and beyond," Hepatology, 43:385-394 (2006). Exhibit 2033 in *Mallinckrodt v. BioVie* IPR2018-00974, filed by BioVie on Mar. 7, 2019.
Schindler et al., "Albumin substitution improves urinary sodium excretion and diuresis in patients with liver cirrhosis and refractory ascites," Journal of Hepatology, 31:1132 (1999). Exhibit 2036 in *Mallinckrodt v. BioVie* IPR2018-00974, filed by BioVie on Mar. 7, 2019.
De Franchis et al., "Revising consensus in portal hypertension: report of the Baveno V consensus workshop on methodology of diagnosis and therapy in portal hypertension," Journal of Hepatology, 53(4):762-768 (2010). Exhibit 2037 in *Mallinckrodt v. BioVie* IPR2018-00974, filed by BioVie on Mar. 7, 2019.
De Franchis et al., "Expanding consensus in portal hypertension: Report of the Baveno VI Consensus Workshop: Stratifying risk and individualizing care for portal hypertension," Journal of Hepatology, 63(3):743-752 (2015). Exhibit 2038 in *Mallinckrodt v. BioVie* IPR2018-00974, filed by BioVie on Mar. 7, 2019.
Transcript of the Deposition of Dr. Paul Gow, dated Feb. 13, 2019. Exhibit 2039 in *Mallinckrodt v. BioVie* IPR2018-00974, filed by BioVie on Mar. 7, 2019, pp. 1-154.
Supplemental Declaration of Dr. Jaime Bosch, MD, PhD Under 37 C.F.R. § 1.68 in Support of Patent Owner's Sur-Reply. Exhibit 2044 in *Mallinckrodt v. BioVie* IPR2018-00974, filed by BioVie on Jun. 28, 2019, pp. 1-13.
Patent Owner's Response Under 37 C.F.R. § 42.120. Paper 15 in *Mallinckrodt v. BioVie* IPR2018-00974, filed by BioVie on Mar. 7, 2019, pp. 1-74.
Patent Owner's Contingent Motion to Amend Under 37 C.F.R. § 42.121. Paper 16 in *Mallinckrodt v. BioVie* IPR2018-00974, filed by BioVie on Mar. 7, 2019, pp. 1-35.
Petitioner's Reply to Patent Owner's Response. Paper 18 in *Mallinckrodt v. BioVie* IPR2018-00974, filed by Mallinckrodt on Jun. 4, 2019, pp. 1-31.
Petitioner's Opposition to Patent Owner's Contingent Motion to Amend. Paper 19 in *Mallinckrodt v. BioVie* IPR2018-00974, filed by Mallinckrodt on Jun. 4, 2019, pp. 1-31.
Patent Owner's Sur-Reply to Petitioner's Reply. Paper 21 in *Mallinckrodt v. BioVie* IPR2018-00974, filed by BioVie on Jun. 28, 2019, pp. 1-37.
Patent Owner's Reply In Support of Its Contingent Motion to Amend Under 37 C.F.R. § 42.121. Paper 22 in *Mallinckrodt v. BioVie* IPR2018-00974, filed by BioVie on Jun. 28, 2019, pp. 1-23.
Patent Owner's Request for Oral Argument. Paper 23 in *Mallinckrodt v. BioVie* IPR2018-00974, filed by BioVie on Jul. 14, 2019, pp. 1-4.
Testino et al., "Type-2 hepatorenal syndrome and refractory ascites: role of transjugular intrahepatic portosystemic stent-shunt in eighteen patients with advanced cirrhosis awaiting orthotopic liver transplantation," Hepatogastroenterology, 50(54):1753-5 (2003).

\* cited by examiner

TREATMENT OF ASCITES

RELATED APPLICATIONS

This application is a continuation of U.S. patent application Ser. No. 15/491,613, filed Apr. 19, 2017, which is a continuation of U.S. patent application Ser. No. 15/198,050, filed Jun. 30, 2016, now U.S. Pat. No. 9,655,945, which claims the benefit of U.S. provisional patent application 62/321,558, filed Apr. 12, 2016, U.S. provisional patent application 62/267,510, filed Dec. 15, 2015, and U.S. provisional patent application 62/186,638, filed Jun. 30, 2015, each of which is incorporated by reference herein in its entirety.

FIELD

The disclosure is directed to a method for treating ascites patients by administering the peptide drug terlipressin.

BACKGROUND

Ascites is a frequent and life-threatening complication of advanced liver cirrhosis with an expected 40% mortality rate within two years of diagnosis. To date the US FDA has not approved any therapies specifically to treat ascites, although a few drugs (e.g., diuretics) are being used off-label with limited and temporary efficacy. Studies have shown that intravenous (IV) injections of terlipressin every 4 to 6 hours in hospitalized patients with type 1 hepatorenal syndrome (HRS) can save their lives. FIRS is the beginning of renal failure and frequently occurs in patients with ascites that has become refractory to treatment with diuretics. Additionally, investigational studies have shown that IV injections of terlipressin every 4 to 6 hours in combination with diuretics may resolve refractory ascites in hospitalized patients and decrease the need for large volume paracentesis (ascites fluid withdrawal by needle). However these intermittent high-dose IV injections (typically 1 or 2 mg in a single dose) carry a high risk of side-effects. More recent studies with hospitalized HRS patients indicate that a continuous infusion of terlipressin can achieve similar efficacy to intermittent injections with a much better safety profile. However to date there have been no published studies of using a continuous low-dose infusion terlipressin to manage ascites in non-hospitalized patients with cirrhosis.

Accordingly, the inventors have identified a need in the art for a method to treat ascites patients on an outpatient basis and potentially avoid or delay the need for hospitalization due to HRS or other life-threatening complications.

SUMMARY

In one aspect, the disclosure is directed to a method for treating a patient diagnosed with ascites due to liver cirrhosis. The method including administering terlipressin or salt thereof as a continuous infusion. The condition of the patient may not have progressed to HRS.

In another aspect, the disclosure is directed to a method for reducing the volume of ascitic fluid during a paracentesis procedure in an ascites patient. The method includes administering terlipressin or salt thereof as a continuous infusion.

In yet another aspect, the disclosure is directed to a method for reducing the number of monthly paracentesis procedures in an ascites patient. The method includes administering terlipressin or salt thereof as a continuous infusion.

Still further, the disclosure is directed to a method for improving renal function in an ascites patient. The method includes administering terlipressin or salt thereof as a continuous infusion. In various aspects, the improvement in renal function includes one or more of the following: a reduction in serum creatinine concentration, an increase in plasma sodium concentration, an increase in urinary sodium excretion, and a decrease in urea concentration in serum.

The disclosure is also directed to a method for correcting hyponatremia in an ascites patient. The method includes administering to the patient terlipressin or salt thereof as a continuous infusion.

In a further aspect, the disclosure is directed to a method for improving the health status of the ascites patient with liver cirrhosis due to hepatitis C. The method includes method comprising administering a hepatitis C antiviral medication in combination with administering terlipressin or salt thereof as a continuous infusion.

In another aspect, the disclosure is directed to a method of improving the Model for End-Stage Liver Disease (MELD) score of an ascites patient. The method includes administering terlipressin or salt thereof with a continuous infusion.

In each of the aspects of the invention, the condition of the patient may not have progressed to HRS. Also, the terlipressin dose may range from about 1.0 mg to about 12.0 mg per day, and the terlipressin dose may be escalated over the course of the therapy. In addition, the terlipressin may be administered for a time period of about 1 day to about 12 months. Further, the continuous terlipressin may be administered with an ambulatory infusion pump.

DESCRIPTION

Terlipressin is a synthetic vasopressin that is approved in many countries outside of the United States to treat the life-threatening complications of cirrhosis, including hepatorenal syndrome (HRS) and esophageal bleeding (EVB). Its use is limited to the hospital setting due to its short half-life (26 minutes) (Nilsson, et al., 1990), necessitating its administration as an intravenous bolus usually every 4 to 6 hours. Additionally, terlipressin can cause side effects in up to 40% of patients. Severe side effects—including myocardial infarction, arrhythmia and intestinal infarction—can require discontinuation of treatment in up to 10% of the patients (Angeli, 2011). Indeed, due to the rapid vasoconstrictor properties, IV bolus dosed terlipressin must be used with caution in patients with severe asthma, severe hypertension, advanced atherosclerosis, cardiac dysrhythmias, and coronary insufficiency.

In one aspect, the disclosure is directed to the administering terlipressin or a salt thereof for the treatment of patients suffering from ascites due to, for example, advanced liver cirrhosis. These patients are typically non-hospitalized (or ambulatory) and may include patients whose condition has not progressed to type 2 HRS (ambulatory HRS patients) or type 1 HRS (requiring hospitalization). Treatment includes a continuous infusion of terlipressin by means of a pump device, typically a portable ambulatory pump, for a period of several hours, lasting up to days, weeks, or months. The treatment is effective at reducing or resolving ascites disease on, for most patients, an outpatient basis.

Patients with cirrhosis exhibiting type 1 hepatorenal syndrome (HRS-1) have been safely treated with terlipressin administered continuously. Dosage ranged from 2.0-12.0 mg per 24 hours (Angeli, et al., 2009: 2-12 mg/24 h; Gerbes, 2009: starting dose 3 mg/day; Robertson, et al., 2014: 3 mg/day; Ding, 2013: 4 mg/day; Cavallin 2015: 3-12 mg/day). However, none of these studies have either evaluated or reported an effect of terlipressin infusion on ascites burden or the effect of continuous infusion terlipressin on patients whose condition have not progressed to HRS.

Ambulatory pumps are commonly used to infuse parenteral drugs directly into the bloodstream via catheters to increase efficacy and/or decrease toxicity. This has been found to be safer than some approved terlipressin drug therapy that require the administration of terlipressin to hospitalized hepatorenal syndrome (HRS) patients and esophageal bleed (EVB) patients using slow bolus IV injections. Accordingly, in one aspect of the disclosure, terlipressin is administered continuously by a pump at a dosage rate of about 0.5 mg to about 20 mg every 24 hours, more particularly for example, about 1 mg to about 12 mg every 24 hours, more particularly for example, about 5 to about 15 mg every 24 hours, or for instance, about 1, 2, 3, 4, 5, 6, 7, 8, 9, 10, 11, 12, 13, 14, 15, 16, 17, 18, 19, or 20 mg every 24 hours. Administration can continue for, typically, at least about one day and may continue for about 12 months or longer as necessary to bridge a patient until a transplant is available. For example, the administration can continue for about 1 day, 2 days, 3 days, 4 days, 5 days, 6 days, one week, two weeks, three weeks, one month, two months, three months, six months, 9 months or twelve months. In some instances, the dose of terlipressin escalates over the course of the therapy. For example, patients may begin therapy at 2 mg/day, and be increased to 3 mg/day or up to 12 mg/day over the course of treatment.

Accordingly, in various aspects, the disclosure is directed to a method for treating a patient diagnosed with ascites due to liver cirrhosis. The method can improve renal function in an ascites patient and reduce the volume of ascitic fluid during paracentesis procedure in the patient. Still further, the method can be used for reducing the risk of spontaneous bacterial peritonitis, improving the Model for End-Stage Liver Disease (MELD) score of an ascites patient and/or correcting hyponatremia in an ascites patient. In another aspect, the method disclosed herein can be used in combination with hepatitis C antiviral medications to improve the health status of the ascites patient with liver cirrhosis due to hepatitis C. In each case terlipressin or salt thereof is administered with a continuous infusion pump. In each of these aspects, the patient's ascites condition may not have progressed to hepatorenal syndrome.

In addition, the determination of the presence, progression, or improvement of disease can be determined by measuring one or more of the following: serum creatinine concentration, plasma sodium concentration, urinary sodium excretion, and urea concentration in serum. For example, an improvement in renal function that indicates an improvement in disease condition includes one or more of the following: a reduction in serum creatinine concentration, an increase in plasma sodium concentration, an increase in urinary sodium excretion, a decrease in urea concentration in serum of disease.

The use of ambulatory pump delivery of continuous infusion of terlipressin would avoid the need for patient hospitalization and make such therapy available to the vast majority of ascites patients who have not yet been hospitalized for severe complications that often follow advanced ascites, such as post-paracentesis circulatory dysfunction, HRS, EVB, hepatic encephalopathy, spontaneous bacterial peritonitis and other life-threatening conditions.

EXAMPLES

The following are provided for exemplification purposes only and are not intended to limit the scope of the disclosure described in broad terms above.

Example 1: Treatment of Ascites with Continuous Infusion Pump Terlipressin Therapy 15 subjects that are to be confirmed to have ascites, but not type 1 or type 2 HRS, due to liver cirrhosis will be administered continuous low dose (escalating from 2.0 to 3.0 mg per 24 hours) terlipressin via ambulatory infusion pump. These patients are expected to experience a decrease the severity of ascites and the accumulation of ascites fluid over the course of treatment ranging from 1 day to 28 days. This method is also expected to reduce the number of paracentesis procedures required to remove ascitic fluid over a 28-day period, compared to the 28-day period prior to treatment inception, and some patients should avoid paracentesis altogether. Additionally the average amount of fluid withdrawn after beginning continuous infusion pump terlipressin therapy should be significantly less than prior to the start of treatment. Furthermore the improvement in patient health status can be achieved safely with no serious side effects. Accordingly, continuous infusion pump (CIP) terlipressin represents a potentially life-saving solution for these seriously ill patients who are still ambulatory (have not yet been administered to the hospital for treatment) and have not developed type 1 or type 2 HRS.

Example 2: Treatment of Ascites with Continuous Infusion Pump Terlipressin Therapy Six FIRS patients treated with continuous infusion terlipressin were evaluated for improvement in acsites. All six patients had diuretic intractable or refractory ascites (5 of 6 with hyponatremia). The patients were evaluated for the following parameters before, during and after treatment: number of paracentesis procedures per month, volume of ascites removed, weight, serum sodium, urinary sodium excretion, serum creatinine, serum urea, and whether diuretics were included in the treatment regimen. None of the six patients had a complete set of data for all parameters. The effect of continuous infusion terlipressin on each parameter is presented in Tables 1-7.

Reduction in Frequency of Paracentesis and Fluid Volume During Therapy

The average number of monthly paracentesis procedures decreased from three prior to initiation of continuous infusion therapy to two during therapy, and the average monthly ascites fluid volume removed was reduced by 55%.

TABLE 1

| Patient # M/F | Max. Dose (mg/day) | Duration (days) | Paracenteses/Month | | | Volume Fluid Removed/Month (L) | | |
|---|---|---|---|---|---|---|---|---|
| | | | Before | During | % Change | Before | During | % Change |
| 1 M | 12 | 63 | 1 | 0 | −100% | — | — | — |
| 2 F | 12 | 195 | 8 | 6 | −25% | 80 | 42 | −48% |
| 3 M | 3 | 10 | 4 | 2 | −50% | 40 | 14 | −65% |
| 4 M | 10 | 11 | 2 | 3 | 50% | 14 | 9 | −36% |
| 5 F | 3 | 22 | 3 | 2 | −33% | 21 | 6 | −71% |
| 6 F | 2 | 12 | 1 | 0 | −100% | 2 | 0 | −100% |
| Average (excludes patient #1): | | | 3 | 2 | −32% | 31 | 14 | −55% |

"—" indicates missing data

Reduction in Body Weight During Therapy

Average body weight per patient, a proxy for ascitic fluid accumulation in the abdominal cavity, decreased by 11% or 9 kg (~19.8 lbs).

TABLE 2

| Patient # M/F | Max. Terli. Dose (mg/day) | Duration (days) | Body Weight (kg) Before | During | % Change | After |
|---|---|---|---|---|---|---|
| 1 M | 12 | 63 | 83 | 74 | −11% | 74 |
| 2 F | 12 | 195 | 64 | 71 | 11% | — |
| 3 M | 3 | 10 | 128 | 99 | −23% | 128 |
| 4 M | 10 | 11 | 60 | — | — | — |
| 5 F | 3 | 22 | 71 | 64 | −10% | 77 |
| 6 F | 2 | 12 | 64 | 55 | −14% | 68 |
| Average (excludes Patient #4): | | | 82 | 73 | −11% | 87 |

"—" indicates missing data

Requirement for Diuretics for Effect on Ascites

During treatment, improvement of ascites was seen without diuretics in four of six patients.

TABLE 3

| Patient # M/F | Max. Terli. Dose (mg/day) | Treatment Diuretics Before | Diuretics During | % Change Paracentesis per Month | Volume Fluid Removed | Body Weight |
|---|---|---|---|---|---|---|
| 1 M | 12 | A | A | −100% | — | −11% |
| 2 F | 12 | A | None | −25% | −48% | 11% |
| 3 M | 3 | F + A | None | −50% | −65% | −23% |
| 4 M | 10 | F + A | None | 50% | −36% | — |
| 5 F | 3 | A | None | −33% | −71% | −10% |
| 6 F | 2 | F + A | F + A | −100% | −100% | −14% |
| | | | Average: | −32% | −55% | −11% |

F = furosemide;
A = anti-aldosteronic drug.
"—" indicates missing data.

Increase in Urinary Sodium Excretion During Therapy

The observed improvement in ascites and renal function was further supported by a substantial increase in excretion of sodium into the urine. The average urinary sodium increased from 7 to 127 mEq/24 h in three of sis patients with data recorded before and after starting continuous infusion terlipressin therapy.

TABLE 4

| Patient # M/F | Max. Terli. Dose (mg/day) | Duration (days) | Urinary Na over 24 hours (mEq/24 hr) Before | During | % Change |
|---|---|---|---|---|---|
| 1 M | 12 | 63 | 5 | 46 | 820% |
| 2 F | 12 | 195 | — | 301 | — |
| 3 M | 3 | 10 | — | — | — |
| 4 M | 10 | 11 | 1 | 20 | 1900% |
| 5 F | 3 | 22 | — | 33/140 | — |
| 6 F | 2 | 12 | 16 | 315 | 1869% |
| Average (excludes patients #2, #3, #5): | | | 7 | 127 | 1632% |

"—" indicates missing data

Improvement in Plasma Sodium

Treatment with continuous infusion terlipressin corrected severe hyponatremia in two patients: Plasma Na increased by 15% in patient #4 and by 19% in patient #6. Importantly, after the cessation of therapy, plasma sodium remained normal in patient #6 (data "after therapy" available for one of the two patients).

TABLE 5

| Patient # M/F | Max. Terli. Dose (mg/day) | Duration (days) | Plasma Sodium (mEq/L) Before | During | % Change | After |
|---|---|---|---|---|---|---|
| 1 M | 12 | 63 | 140 | 137 | −2% | — |
| 2 F | 12 | 195 | 125 | 128 | 2% | — |
| 3 M | 3 | 10 | 133 | 136 | 2% | 140 |
| 4 M | 10 | 11 | 123 | 141 | 15% | — |
| 5 F | 3 | 22 | 131 | 128 | −2% | — |
| 6 F | 2 | 12 | 118 | 140 | 19% | 131 |
| | | Average: | 128 | 135 | 5% | 136 |

"—" indicates missing data

Reduction in Blood Urea During Treatment

The concentration of urea in patients' blood serum decreased in all patients by an overall average of 45%. This increase in urea clearance is indicative of improved renal function.

TABLE 6

| Patient # M/F | Max. Terli. Dose (mg/day) | Duration (days) | Serum Urea (mmol/L) Before | During | % Change | After |
|---|---|---|---|---|---|---|
| 1 M | 12 | 63 | 31.1 | 8.8 | −72% | — |
| 2 F | 12 | 195 | 36.6 | 23.2 | −37% | — |
| 3 M | 3 | 10 | 17.0 | 9.1 | −46% | 10.8 |
| 4 M | 10 | 11 | 51.8 | 37.3 | −28% | — |
| 5 F | 3 | 22 | 6.4 | 5.3 | −17% | 10.5 |
| 6 F | 2 | 12 | 20.4 | 6.6 | −68% | 10.0 |
| | | Average: | 27.2 | 15.1 | −45% | 10.4 |

"—" indicates missing data

Reduction in Serum Creatinine

Levels of the metabolic waste product serum creatinine are indicative of renal health. An average decrease of 47% was seen in serum creatinine levels for the treated group of patients. This was consistent with the decrease in serum urea and indicates improved renal function, contributing to a decrease in ascites severity.

TABLE 7

| Patient # M/F | Max. Terli. Dose (mg/day) | Duration (days) | Serum Creatinine (mmol/L) | | | |
|---|---|---|---|---|---|---|
| | | | Before | During | % Change | After |
| 1 M | 12 | 63 | 248 | 189 | −24% | — |
| 2 F | 12 | 195 | 383 | 208 | −46% | — |
| 3 M | 3 | 10 | 233 | 116 | −50% | 122 |
| 4 M | 10 | 11 | 319 | 104 | −67% | — |
| 5 F | 3 | 22 | 68 | 55 | −19% | 55 |
| 6 F | 2 | 12 | 195 | 90 | −54% | 137 |
| | | Average: | 241 | 127 | −47% | 105 |

"—" indicates missing data

All references cited in this disclosure are incorporated herein by reference.

Nilsson, G. et al., 1990. Nilsson G, Lindblom P, OhlPharmacokinetics of Terlipressin After Single i.v. Doses to Healthy Volunteers. Drugs Under Experimental and Clinical Research, Volume 16, pp. 307-314.

Angeli, P., 2011. Terlipressin for Hepatorenal Syndrome: Novel Strategies and Future Perspectives. Frontiers of Gastrointestinal Research, Volume 28, pp. 189-197.

Angeli, P. et al., 2009. Terlipressin Given as Continous Intravenous Infusion Versus Terlipressin Given as Intravenous Boluses in the Treatment of Type 1 Hepatorenal Syndrome (HRS) in Patients with Cirrhosis. Journal of Hepatology, 50 (Supplement 1), p. S73.

Gerbes A L, Huber E, Gülberg V. 2009 Terlipressin for hepatorenal syndrome: continuous infusion as an alternative to i.v. bolus administration. 2009 Gastroenterology. 137(3): 1179; author reply 1179-81

Ding, C. et al., 2013. Hemodynamic effects of continuous versus bolus infusion of terlipressin for portal hypertension: A randomized comparison. Journal of Gastroenterology and Hepatology, 28(7), pp. 1242-1246.

Robertson, M. et al., 2014. Continuous outpatient terlipressin infusion for hepatorenal syndrome as a bridge to successful liver transplantation. Hepatology March 2014. Hepatology, Volume March, pp. 1-2.

Cavallin M, et. al., 2015 Terlipressin Plus Albumin Versus Midodrine and Octreotide Plus Albumin in the Treatment of Hepatorenal Syndrome: A Randomized Trial. Hepatology, 2015 (in press)

Fimiani, B. et al., 2011. The Use of Terlipressin in Cirrhotic Patients with Refractory Ascites and Normal Renal Function: A Multicentric Study. European Journal of Internal Medicine, Volume 22, pp. 587-590.

Krag, A. et al., 2007. Telipressin Improves Renal Function in Patients with Cirrhosis and Ascites Without Hepatorenal Syndrome. Hepatology, 46(6), pp. 1863-1871.

Although various specific embodiments of the present disclosure have been described herein, it is to be understood that the disclosure is not limited to those precise embodiments and that various changes or modifications can be affected therein by one skilled in the art without departing from the scope and spirit of the disclosure.

What is claimed is:

1. A method for treating ascites in a non-hepatorenal syndrome (HRS) patient diagnosed with ascites due to liver cirrhosis, the method consisting of administering a monotherapy of a continuous infusion of terlipressin or salt thereof to the patient at a continuous infusion dose of about 0.8 mg to about 5.0 mg of terlipressin per day, wherein the patient is not hospitalized, and wherein the ascites in the patient is reduced.

2. The method of claim 1, wherein the continuous infusion of terlipressin is administered with an ambulatory infusion pump.

3. The method of claim 1, wherein the administration is provided on an out-patient basis.

4. The method of claim 1, wherein the continuous infusion dose escalates over a treatment duration of about one day to about 12 months.

5. The method of claim 1, wherein the continuous infusion is administered in a dose of about 3 mg of terlipressin per day.

6. The method of claim 1, wherein the patient is not administered diuretics during a treatment duration with terlipressin.

7. The method of claim 1, wherein the patient is further diagnosed with hyponatremia.

8. The method of claim 1, wherein reduced ascites in the patient is indicated by a reduction in the frequency of paracentesis procedures after beginning a treatment duration with terlipressin.

9. The method of claim 1, wherein reduced ascites in the patient is indicated by a reduction in the volume of ascitic fluid that is removed per paracentesis procedure after beginning a treatment duration with terlipressin.

10. The method of claim 1, wherein reduced ascites in the patient is indicated by an increase in urinary sodium excretion during a treatment duration with terlipressin.

11. A method for reducing the accumulation of ascitic fluid in the abdominal cavity in an ascites, non-HRS patient, the method consisting of administering a monotherapy of a continuous infusion of terlipressin or salt thereof to the patient at a continuous infusion dose of about 0.8 mg to about 5.0 mg of terlipressin per day, wherein the patient is not hospitalized, and wherein reducing the accumulation of ascitic fluid in the abdominal cavity of the patient improves the ascites in the patient.

12. The method of claim 11, wherein the terlipressin is administered for a treatment duration of about one day to about 12 months.

13. The method of claim 11, wherein the continuous infusion of terlipressin is administered with an ambulatory infusion pump.

14. The method of claim 11, wherein the administration is provided on an out-patient basis.

15. The method of claim 11, wherein the continuous infusion dose escalates over a treatment duration of about one day to about 12 months.

16. The method of claim 11, wherein the continuous infusion is administered in a dose of about 3 mg of terlipressin per day.

17. The method of claim 11, wherein the patient is not administered diuretics during a treatment duration with terlipressin.

18. The method of claim 11, wherein the patient is further diagnosed with hyponatremia.

* * * * *